United States Patent [19]

Thomas et al.

[11] Patent Number: 5,130,237
[45] Date of Patent: Jul. 14, 1992

[54] SUBSTRATE CONVERSION WITH AN ENZYME IMMOBILIZED ON AN ULTRAFILTRATION MEMBRANE

[75] Inventors: Ronald L. Thomas, Clemson, S.C.; Daniel L. McKamy, Columbus, Ohio

[73] Assignee: Clemson University, Clemson, S.C.

[21] Appl. No.: 367,727

[22] Filed: Jun. 19, 1989

[51] Int. Cl.$^5$ .................. C12P 19/20; C12N 11/14; C12N 11/08; C12M 1/40
[52] U.S. Cl. ............................ 435/96; 426/50; 426/52; 435/41; 435/98; 435/176; 435/180; 435/288; 435/803
[58] Field of Search .............. 435/41, 96, 176, 180, 435/288, 803; 426/50, 52

[56] References Cited

U.S. PATENT DOCUMENTS

| | | | |
|---|---|---|---|
| 4,001,085 | 1/1977 | Keyes | 435/176 |
| 4,033,822 | 7/1977 | Gregor | 435/180 X |
| 4,266,026 | 5/1981 | Breslau | 435/182 X |
| 4,716,044 | 12/1987 | Thomas et al. | 426/51 |
| 4,897,465 | 1/1990 | Cordle et al. | 530/387 |
| 4,957,890 | 9/1990 | Wieserman et al. | 435/176 X |
| 4,962,073 | 10/1990 | Martin et al. | 435/176 X |

*Primary Examiner*—David M. Naff
*Attorney, Agent, or Firm*—Dority & Manning

[57] ABSTRACT

A process is disclosed for chemically converting a substrate into its reaction products and immediately thereafter physically separating the reaction products in a continuous operation. The process is carried out with a bioreactor having an ultrafiltration membrane containing an immobilized chemical agent which is preferably an enzyme. The bioreactor is prepared by securing an ultrafiltration membrane to an inside wall of a porous tubular support and chemically bonding an enzyme to an inner surface of the membrane. The enzyme is preferably bonded to the membrane by chelation and the membrane may be a polymeric membrane or a metal oxide membrane. To convert a substrate, a substrate-containing feed stream is preferably flowed tangentially along the inner surface of the membrane containing the immobilized enzyme. Sufficiently small reaction products filter through pores of the membrane and larger reaction products are retained by the membrane. In a preferred embodiment, contacting of fresh fruit juice with pectinase immobilized on the membrane results in pectinase treatment or the juice and immediate extraction and clarification of the juice. In another embodiment, the enzyme immobilized is glucoamylase and corn dextrins are converted to reducing sugars.

8 Claims, 6 Drawing Sheets

SUBSTRATE CONVERSION WITH AN ENZYME IMMOBILIZED ON AN ULTRAFILTRATION MEMBRANE

BACKGROUND OF THE INVENTION

The present invention relates to the immobilization of chemical agents on membranes for the chemical conversion of a substrate into its reaction products and physical separation immediately thereafter of those reaction products.

Applicant in U.S. Pat. No. 4,716,044 disclosed an improved process for obtaining juice from fruit. A puree of fruit is pumped through an elongated, rigid, porous housing having a food grade ultrafiltration membrane secured along inside surfaces thereof. Juices from the puree filter through the membrane and porous walls of the housing as the retained pulp exits the system in a form suitable for human consumption. The puree is optionally pretreated with enzymes to decrease viscosity by chemically converting the substrate prior to physical separation.

It is well known in the food industry to enzymatically treat the foods being processed. In order to retain the enzymes needed to catalyze the chemical reactions common in food processing and other applications, it has become the norm in the art to immobilize enzymes onto insoluble carriers or matrices.

For example, U.S. Pat. No. 4,033,822 discloses the coupling of enzymes to polymeric ultrafiltration membranes. Enzymes are fixed under pressure to the inner surfaces of pores within the membrane. The diameter of the pores are determined by the size of the enzyme and the size of the substrate to be treated. The pores must be larger than the substrate so that it may pass therethrough for catalysis by the enzyme contained therein. Thus, the membrane of the '822 patent provides merely a means for exposure of the substrate to the enzyme. Immediate physical separation is precluded.

Other means of immobilizing catalysts, including enzymes, onto insoluble carriers have included the chelation of the enzymes onto metal oxides as described in U.S. Pat. Nos. 3,912,593 and 4,016,293. While these enzymes are rendered insoluble for the batch or continuous feed treatment of substrates, once again, immediate physical separation is not provided for.

Further examples of the immobilization of enzymes onto insoluble supports include U.S. Pat. No. 4,511,654 which discloses the two-step process of contacting a feed stock containing a substrate with an enzyme immobilized on a solid support followed by physical separation as by passing the pretreated solution through an ultrafiltration membrane. U.S. Pat. No. 4,430,348 describes a ceramic monolith having an active enzyme immobilized thereon through which is passed fermenting beer for the production of low calorie beer.

The present invention is directed to the immobilization of chemical agents onto membranes which are formed-in-place within the matrix of a rigid, porous housing. While numerous chemical agents which will induce a chemical reaction of a substrate into reaction products are within the scope of the present invention, the present discussion focuses primarily on enzymes which are immobilized on metallic membranes by chelation thereto. Such enzymes serve to induce a chemical reaction of a substrate by catalysis. A substrate in accordance with the present invention is any substance on which the given chemical agent immobilized on the membranes may act to induce in some manner a chemical reaction thereof. Thus, a feed stream containing the substrate passes through the housing wherein the substrate is chemically converted as by catalysis upon contact with an enzyme and is physically separated as the product passes through the membrane and the porous walls of the housing while the retentate passes through an exit end of the housing for separate collection.

The process of the present invention may be arranged as either a one-pass, continuous feed system or a recirculating system with the retentate which passes through the exit end of the housing recirculated back into the feed stream as the permeate is separately collected. When arranged for the immobilization of the chemical agent within the housing, preferably both the retentate and the permeate of the present process recirculate until maximum immobilization is achieved.

The retentate and permeate are physically separated generally by size as the smaller permeate products pass through the ultrafiltration membrane and porous housing and the larger retentate is precluded from filtering through the membrane and therefore continues along the length of the tubular housing. However, as is generally known in the art, ultrafiltration membranes may also act to separate species by charge such that a product, although sufficiently small to pass through the membrane, which has a like charge to that of the membrane, will be repulsed from the membrane and maintained in the retentate. Such a charge separation of the products by the membrane is also within the scope of the present invention.

SUMMARY OF THE INVENTION

It is thus an object of the present invention to provide a process for chemical conversion of a substrate into its reaction products followed by the immediate physical separation by size of those reaction products.

Another object of the present invention is to provide an insoluble porous support for the immobilization of a chemical agent for conversion of a substrate into its reaction products and for physical separation of the reaction products immediately thereafter.

A further object of the present invention is to provide an improved process for the production of fruit juices from fresh fruit by enzyme treatment of a fruit puree immediately followed by extraction and clarification of the juice.

Yet another object of the present invention is to provide a continuous feed system for the chemical conversion of a substrate into its reaction products by enzymatic treatment and the physical separation by ultrafiltration of those reaction products.

It is still another object of the present invention to provide a system for treatment of substrates by enzymes wherein the enzymes are recoverable in that they may be used repeatedly for treatment of further substrates.

These, as well as other objects, are achieved by providing an elongated, tubular, rigid, porous housing which has an ultrafiltration membrane secured along its inside surfaces, immobilizing a chemical agent onto the inside surfaces of the housing by chemical bonding to the membrane and passing a feed stream containing a substrate through the tubular porous housing such that the chemical agent immobilized on its inside surfaces induces a chemical reaction of the substrate, converting the substrate into reaction products with physical separation by size or charge following immediately thereafter. The process may be arranged as a single pass, continuous feed system wherein the permeate which passes through the walls of the porous housing and the retentate which passes through an exit end of the housing are collected separately. Alternatively, the retentate may recirculate allowing for a shorter tubular housing as, generally, in a single pass system the housing must be of sufficient length to present ample surface area for the extraction of the permeate from the feed stream. The permeate includes those reaction products which are sufficiently small such that they pass through the membrane and the porous housing while the retentate includes those larger products which, because of their size, are retained by the membrane. The retentate may also be defined as those products having a charge which is repulsed by the membrane causing retention thereof within the feed stream. As physical separation is more common than charge separation, the present discussion will focus primarily on the physical separation of the reaction products of the substrate by size. However, charge separation is within the scope of the present invention.

The process of the present invention provides for a tangential flow of the substrate through the tubular porous housing. This flow provides a cleaning action through the length of the tube which precludes the larger reaction products produced by the chemical reaction of the substrate induced by the chemical agent immobilized within the tube from blocking the pores of the housing and precluding the passage of the smaller products therefrom. Rather the chemical agent within the housing acts on the substrate in the feed stream, converting it into its reaction products with, generally, the smaller products filtering out of the housing and the larger products being forced with the feed stream through the housing to an exit end.

The chemical agent preferred for immobilization to the inner walls of the porous housing is a catalyst, most preferably an enzyme, which can catalyze a chemical reaction of the substrate, thereby converting the substrate into its reaction products without itself being chemically converted. Thus, the present discussion will focus on the employment of enzymes in the present system. However, other chemical agents such as antibodies or proteins are within the scope of the present invention so long as the agent can induce a chemical reaction of a substrate, preferably without itself being chemically converted so that it may be employed in a continuous, rather than batch, system.

The preferred membrane for the present invention is a metal oxide membrane which is formed-in-place within the matrix of the porous housing such as that described in U.S. Pat. No. 4,762,619 to Gaddis et al. Metal oxide membranes are preferred, especially when the chemical agent employed is an enzyme or some other nitrogen-containing organic compound, because the metallic membranes may be chelated by the chemical agent. Chelation, as opposed to other forms of chemical bonding, does not greatly reduce the activity of the chelating agent which, in this case, is the enzyme or other chemical agent. Other membranes, including polymeric membranes, may be employed so long as the required chemical agent may be bound to the surface of the membrane for inducing a chemical reaction of a substrate followed by a physical separation of the products of that reaction. One example of an available membrane formed-in-place within the matrix of a porous housing which may be used in accordance with the present invention is the zirconium oxide-polyacrylic acid membrane disclosed by Gaddis et al in U.S. Pat. No. 4,762,619.

The system is preferably operated as a recirculating batch system during enzyme immobilization. That is, both the concentrate (retentate) and permeate lines are recirculated. The enzyme solution circulating through the system is maintained at a pH approximating the pH of the isoelectric point of the given enzyme. The immobilization of enzymes onto the metallic membranes is independent of temperature, velocity, pressure, and membrane permeability, depending only on the pH of chelation.

BRIEF DESCRIPTION OF THE DRAWINGS

The construction design to carry out the invention will be hereinafter described together with other features thereof.

The invention will be more readily understood from a reading of the following specification and by reference to the accompanying drawings forming a part thereof, wherein examples of the invention are shown and wherein.

DETAILED DESCRIPTION OF PREFERRED EMBODIMENTS

The use of formed-in-place metallic membranes for fruit juice processing was disclosed by the applicant in U.S. Pat. No. 4,716,044. The metallic membranes formed-in-place in a tubular, porous stainless steel support were used to produce clarified apple juice directly from apple purees in a single pass operation which eliminated the need for conventional pressing. Preferably, the purees were pretreated in a conventional batch treatment manner by exposure to enzymes in order to reduce viscosity. Such a conventional enzyme treatment of biological substrates is generally employed in order to catalyze a chemical reaction of the substrates converting them into their respective reaction products.

The present invention is directed to a system having ultrafiltration membranes formed-in-place within the matrix of a porous support with chemical agents chemically bound onto the metallic membrane thereby avoiding the need for a pretreatment step and allowing for a one-pass continuous system for chemical conversion of a substrate into its reaction products followed immediately thereafter by physical separation of those reaction products by size or charge. Alternatively, the feed stream may recirculate through the system as the permeate is continuously collected. Preferably, enzymes are employed which may be chelated onto metallic ultrafiltration membranes for catalysis of the substrate chemically converting it into its reaction products.

Figure 1:
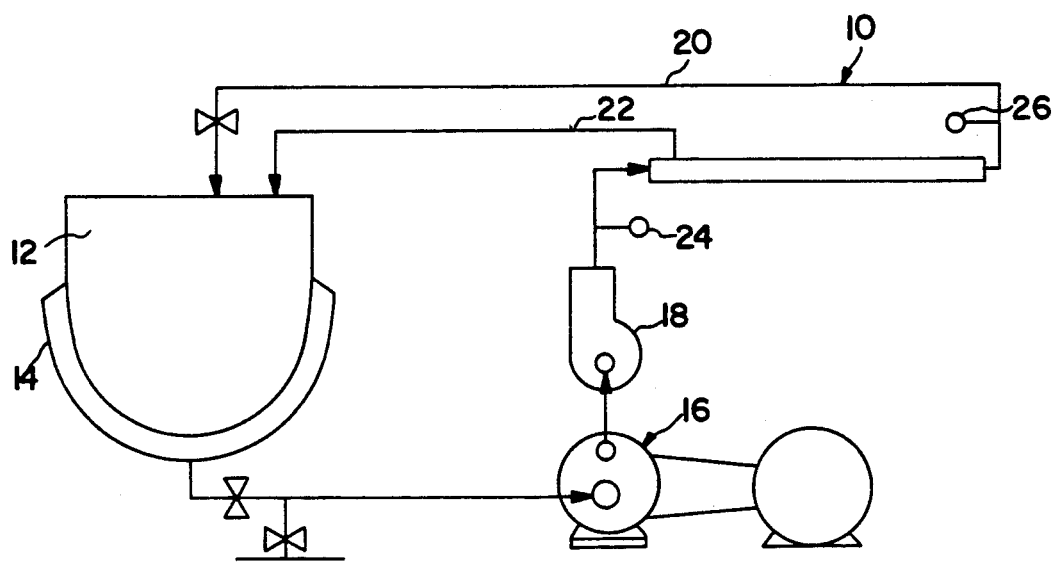
FIG. 1 is a schematic illustration of the ultrafiltration membrane system of the present invention as assembled for enzyme immobilization.

Referring to the figures of the drawings, FIG. 1 is a schematic representation of the ultrafiltration membrane system of the present invention as arranged for enzyme immobilization. The ultrafiltration membrane support of the present invention, represented generally at 10 in FIG. 1, is preferably an elongated, tubular, rigid, porous housing, most preferably a sintered stainless steel tube. Preferably, metallic oxide membranes are formed-in-place within the matrix of the sintered tube. As is shown in FIG. 1, the system preferably operates as a recirculating batch system during enzyme immobilization. An enzyme solution is pumped from a kettle 12, which is steam jacketed as at 14, by diaphragm pump 16 to centrifugal pump 18 which feeds the solution to the metallic ultrafiltration membranes. Both concentrate (retentate) and permeate lines are recirculated from the membrane to the kettle. Pressure gauges 24 and 26, upstream and downstream from the membranes, respectively, monitor the pressure drop.

Generally, the metallic ultrafiltration membranes are prepared for immobilization by washing with an acid solution at a given temperature preferably by recirculation through the system. The acid solution is then drained from the kettle 12 and water is added and circulated to remove any remaining acid. The rinse water is then drained from the system and a buffer solution adjusted to the desired pH is prepared in the kettle. The enzyme is added to the buffer solution, and the solution is circulated through the membranes until maximum immobilization is achieved. The degree of immobilization is measured by periodic protein assays of the buffer solution as is discussed in greater detail below. Additionally, as is shown in the examples below, the immobilization of enzymes in this system is independent of temperature, velocity and pressure as well as membrane permeability and depends only on the pH of the solution, with optimum immobilization occurring at the isoelectric point of the enzyme, that is, the pH at which equivalent amounts of the positively and negatively charged species of the enzymes are found.

Figure 2:
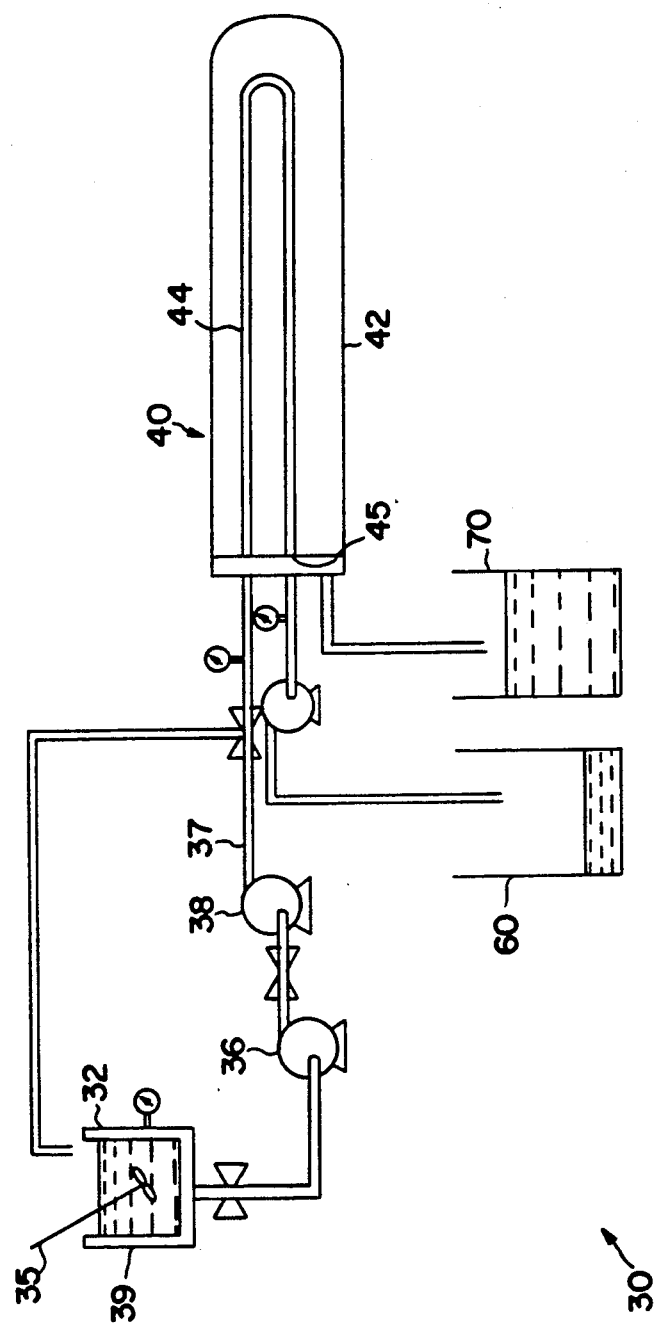
FIG. 2 is a schematic illustration of a preferred arrangement for carrying out the process of the present invention.

After enzyme immobilization, the system may be converted to a continuous feed process 30 such as illustrated in FIG. 2. The ultrafiltration system 40 of the process is generally a bioreactor for chemically converting a substrate into its reaction products and physically separating the reaction products. While the bioreactor is described in greater detail below, it is most generally formed of a porous support of predetermined size and length. Ultrafiltration membranes are deposited along a surface of the support and chemical agents are chemically bound to the membranes. A feed stream containing the substrate for conversion tangentially flows over the surface such that the chemical agents bound onto the membranes induce a chemical reaction of the substrate converting it into its reaction products with, generally, sufficiently small reaction products passing through the ultrafiltration membranes and the porous support and larger reaction products being retained by the ultrafiltration membranes. The smaller reaction products which pass through the membranes in the support and the larger reaction products which are retained by the membranes are collected separately. Alternatively, as discussed above, the reaction products may be physically separated by charge with the products, regardless of size, having a like charge to that of the membrane being repulsed therefrom and retained within the feed stream and the products having a charge opposite to that of the membrane (and sufficiently small to pass through the membrane) being attracted thereto and passing through the porous housing by the attraction to the membrane which is deposited throughout the interstitial spaces of the housing.

More specifically, the support is an elongated, tubular, rigid, porous housing with metal oxide ultrafiltration membranes deposited along its inside surfaces. Most preferably, enzymes are chelated onto the metal oxide membrane. A feed stream containing the substrate is passed through the tubular housing contacting the inside surfaces such that the enzymes chelated onto the membranes catalyze a chemical reaction of the substrate, chemically converting it into its reaction products with sufficiently small reaction products passing through the walls of the tubular housing and larger reaction products being retained therewithin.

Looking to the entire process, the feed stock of substrate to be processed may be preliminarily stored in vat 32 wherein temperature is controlled by steam or cooling water introduced into jacket 34. Depending on the preprocessing viscosity of the stock, it may optionally be mixed as by agitator 35. The substrate feed is then pumped as by pumps 36 and 38 through conduit 37 into the ultrafiltration membrane system indicated generally at 40. In a preferred arrangement, pump 36 is a centrifugal suction booster pump to remove feed stock from vat 32 while pump 38 is a diaphragm pressure pump to pressurize stock fed to the ultrafiltration system 40. Any suitable pump arrangement may, however, be employed so long as predetermined pressures and feed flow are achievable thereby.

Ultrafiltration system 40 preferably includes a shell 42 that surrounds a rigid, porous, tubular housing 44 located therewithin. The housing is preferably a sintered stainless steel tube. The metallic membranes formed-in-place within the matrix of the porous housing have a chemical agent chemically bound to the surfaces thereof. Preferably, this agent is an enzyme immobilized by chelation to the metallic membranes by the recirculating batch method discussed above. The housing itself should be resistant to operating temperatures and pressures accompanying the ultrafiltration process according to the present invention. Additionally, the housing, while schematically indicated as a continuous length of tubing in FIG. 2, may, if desired, be represented by a plurality of separate modular housings joined together to define a continuous passageway between an entrance and an exit end with separate outer shells provided for each separate housing. Such an arrangement would allow for a plurality of porosities such that reaction products of various sizes may be filtered through correspondingly sized pores at separate points along the assembly, as well as for the immobilization of varying enzymes or chemical agents at given stages of the system. However, regardless of the employment of a single housing or a series of connected housings, a single pass operation providing for tangential contact of the substrate with the membrane is preferred.

Thus, the substrate contained in vat 32 passes to the ultrafiltration system 40 by conduit 37 into the porous tubular housing 44. Within the housing, the feed stream containing the substrate contacts, preferably tangentially, the enzymes chelated to the metallic membranes which are formed-in-place within the housing. The enzymes catalyze the chemical reaction of the substrate converting the substrate into its reaction products. The smaller products, because they are smaller than the pores defined within the membrane and the walls of the housing, pass through the membrane and the porous walls of the housing and are collected as product within shell 42. The larger reaction products, that is, those which are too large to pass through the membrane and the porous housing, are retained within the housing and pass therefrom at exit end 45. The two streams, the retentate and the permeate, are collected respectively within vats 60 and 70. Thus, a continuous, one-pass process is provided wherein the enzymes are employed for the continuous catalysis of substrate.

Figure 2A:
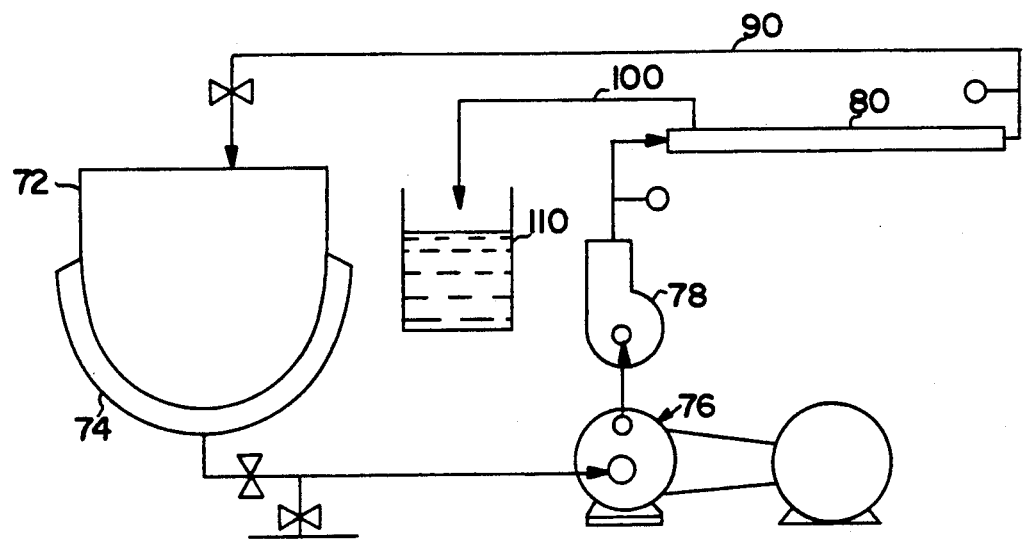
FIG. 2a is a schematic illustration of an alternative arrangement for carrying out the process of the present invention.

Alternatively, a recirculating system, such as that shown in FIG. 2a, may be provided similar to the recirculating batch system used for the immobilization of the enzymes within the housing as discussed above with reference to FIG. 1. Generally, a recirculating batch system is provided with a vat 72 with temperature controlled by steam or cooling water as in jacket 74 for storage of the feed stack. Diaphragm pump 76 feeds the stock from vat 72 to centrifugal pump 78 which feeds the stock to the metallic ultrafiltration membrane system indicated generally as 80. Ultrafiltration system 80, like that of the single pass system discussed above, includes a porous tubular housing, preferably of sintered stainless steel with metallic membranes formed-in-place within the interstitial spaces of the housing and a chemical agent bound to at least the inside surfaces thereof. A shell surrounds the housing to collect the permeate which filters therethrough. However, unlike the tubular housing of the single pass system, the present housing may be relatively short as the retentate in line 90 is continuously recirculated through the system allowing for extraction of the permeate with less surface area. Generally, in a single pass system, a relatively long tube is required in order to provide greater surface area for action of the enzyme or other chemical agent on the substrate. In the present recirculating feed system, it is not necessary that all of the substrate be converted during a single pass through the tube as the feed stock containing the substrate therein is continuously recirculated through the tube until maximum chemical conversion and physical separation is achieved. The permeate in line 100 is drawn off as it passes through the tube and collected in vat 110. Thus, a continuous recirculating production system is provided with the feed stream containing the retentate continuously recirculated from an exit end of the ultrafiltration system to vat 72 and the permeate continuously collected.

A particular ultrafiltration system suitable according to the present invention is provided by DuPont Separation Systems of Seneca, South Carolina and described in the Gaddis et al U.S. Pat. No. 4,200,533. The following examples will facilitate a better understanding of the process of the present invention.

EXAMPLE I

A metallic membrane support was employed which consisted of 1 ¼ inch ×5 feet sintered stainless steel tubes. The tubes were enclosed within stainless steel housings to collect the product. Metallic oxide membranes, supplied by DuPont Separation Systems of Seneca, South Carolina, were formed-in-place within the matrix of the sintered stainless steel tubes.

The metallic membranes were prepared for immobilization of an enzyme thereon by washing with an acid solution. Fifty milliliters of concentrated nitric acid were added to 25 gallons of tap water in a steam-jacketed kettle. The solution temperature was brought to 65° C. and circulated through the membrane in a recirculating batch system such as illustrated in FIG. 1 for thirty minutes. The acid solution was drained from the kettle and fresh tap water was added and circulated through the system to rinse out any remaining acid. The rinse water was drained from the system and 20 liters of a 0.05 molar acetate buffer solution was prepared in the kettle and adjusted to a desired pH ranging from 3.0 to 6.0. The enzyme glucoamylase from Rhizopus mold (Sigma Chemical Company, St. Louis, Missouri) was added to the buffer solution and circulated through the membranes until maximum immobilization was achieved.

The amount of enzyme immobilization was determined by comparing the protein concentration of the buffer solution after addition of the enzyme but before the immobilization procedure was initiated with the protein concentration of the buffer solution after circulation. Maximum immobilization was determined when the protein concentration of the solution became constant.

Protein concentration in the buffer solution was determined by the Bio-Rad Protein Assay (Bio-Rad Chemical Division, South Richmond, California). The protein concentration was assayed by placing 0.1 milliliter of each sample in clean, dry test tubes. The blank was prepared by using 0.1 milliliter of the sample buffer solution. Then five milliliters of diluted dye reagent was added to each test tube, and the contents were vortexed at moderate speed. After 15 minutes the contents of each tube were transferred to 13×100 millimeter round, matched cuvettes, and the absorbance at 595 nanometers was recorded for each sample. The absorbance readings were compared to a standard curve and the protein concentration determined.

Figure 3:
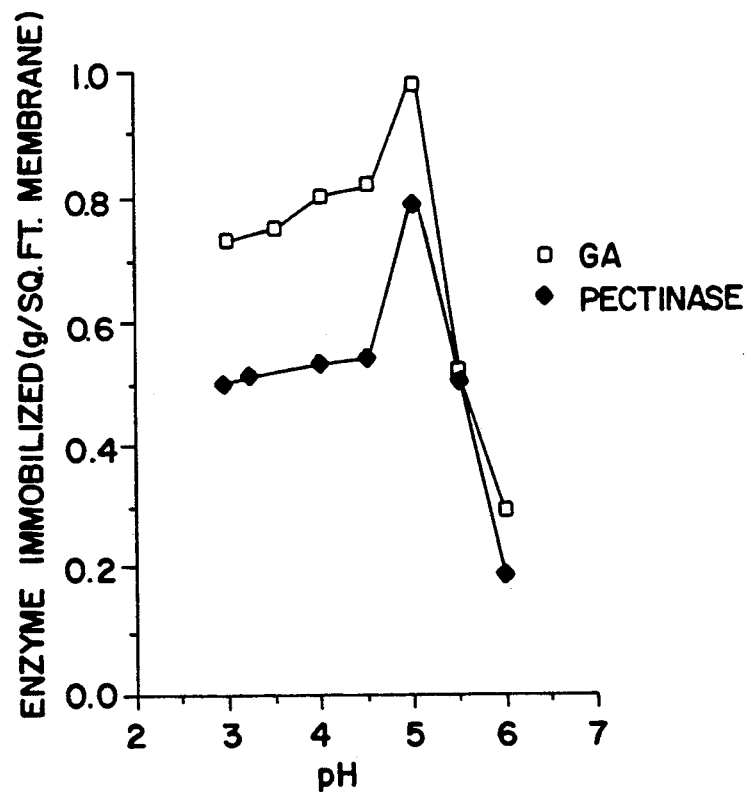
FIG. 3 graphically illustrates the effect of pH on the immobilization of glucoamylase and pectinase on metallic membranes.

After immobilization, the enzyme solution was drained from the kettle, and a fresh buffer solution at the same pH was circulated through the system to remove any enzyme not immobilized. The protein concentration of this wash buffer solution was determined and used in correcting the calculation of total enzyme immobilized. Glucoamylase was immobilized at temperatures of 25° C. and 37° C., velocities of 7.3 feet/second and 20 feet/second, and at pressures of 30, 100 and 200 psi. However, immobilization of glucoamylase was found to be independent of temperature, velocity and pressure and to depend only on the pH of chelation. The greatest amount of glucoamylase immobilized was at pH 5.0 and was 0.98 grams per square foot of membrane as is shown in FIG. 3.

EXAMPLE II

The metallic membranes of Example I were prepared for immobilization of an enzyme thereon by the method of Example I. A 20 liter 0.05 molar acetate buffer solution was prepared in the kettle and adjusted to a desired pH ranging from 3.0 to 6.0. The enzyme pectinase from *Aspergillus niger* (Sigma Chemical Company, St. Louis, Missouri) was added to the buffer solution and circulated through the membranes until maximum immobilization was achieved. The amount of enzyme immobilization was determined by the protein assay method of Example I. After immobilization, the enzyme solution was drained from the kettle, and a fresh buffer solution at the same pH was circulated through the system to remove any enzyme not immobilized. Again, the protein concentration of this wash buffer solution was determined and used in correcting the calculation of total enzyme immobilized. Pectinase was immobilized at temperatures of 25° C. and 37° C., velocities of 7.3 feet/second and 20 feet/second, and at pressures of 30, 100 and 200 psi. However, immobilization of pectinase was found to be independent of temperature, velocity and pressure and to depend only on the pH of chelation. The greatest amount of pectinase immobilized was at pH 5.0 and was 0.79 gram per square foot of membrane as is shown in FIG. 3.

EXAMPLE III

The activity of the pectinase immobilized in Example II at a pH of 5.0 was determined by challenging the enzyme-coated membrane with a 0.1 percent apple pectin solution. The performance, expressed as membrane permeability, was compared to the same membrane without immobilized pectinase.

Figure 4:
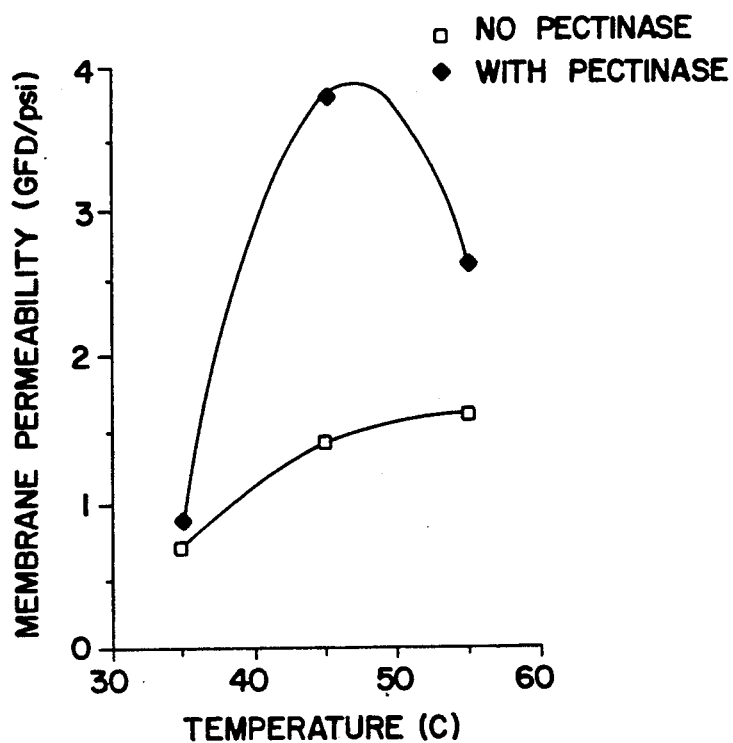
FIG. 4 graphically illustrates the permeability of metallic membranes on a 0.1 percent pectin feed solution with and without pectinase immobilized thereon.

Twenty grams of apple pectin (Sigma Chemical Company, St. Louis, Missouri) were dissolved in 20 liters of a 0.05 molar acetate buffer solution at a pH of 3.5. The apple pectin solution was circulated through the membrane system at 30 psi and at temperatures of 35° C., 45° C. and 55° C. The permeabilities of the enzyme-coated and standard membranes were compared at each temperature. The results are shown in FIG. 4. The membrane with immobilized pectinase showed an improvement in membrane performance at all temperatures with the optimum increase occurring at 45° C. At 45° C., immobilized pectinase improved membrane performance by 271 percent suggesting the enzyme to be acting as an antifoulant to maintain higher membrane permeability.

EXAMPLE IV

The optimum temperature for immobilized glucoamylase activity as immobilized by the method of Example I was determined by examining the conversion of corn dextrins type I (Sigma Chemical Company, St. Louis, Missouri) to reducing sugars. Four hundred grams of corn dextrin were dissolved in 40 liters of a 0.05 molar acetate buffer solution at pH 4.5 and circulated through the ultrafiltration membrane system at temperatures between 30° C. and 70° C. The retentate (feed) line was recirculated to the steam-jacketed feed tank and the permeate line was directed to a fivegallon plastic bucket where the product was collected. Permeate and retentate samples were taken at each temperature and analyzed for reducing sugars and total carbohydrate. The total carbohydrate content of each feed and permeate sample taken during dextrin hydrolysis was analyzed by taking 2 milliliters of suitably diluted sample containing between 5 and 75 micrograms per milliliter total carbohydrate pipetted into clean, dry test tubes. One milliliter of a five percent aqueous phenol solution was pipetted into each tube. Five milliliters of concentrated sulfuric acid was then added rapidly to each tube, and each tube was vortexed briefly. The tubes were left at room temperature for 10 minutes and vortexed again. The tubes were then placed in a 25° C. water bath for 15 minutes. The contents of each tube were then transferred to a 13×100 millimeter round, matched cuvette. The absorbance of each sample was measured at 490 nanometers and compared to a standard curve. Two milliliters of sample buffer solution was used in preparing the sample blank.

Figure 5:
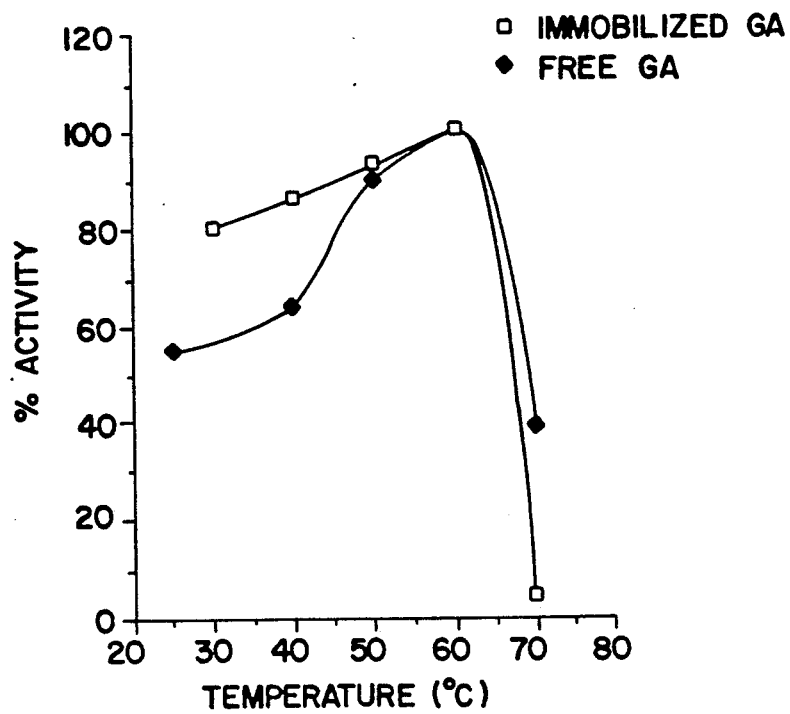
FIG. 5 graphically illustrates the temperature optimum of glucoamylase immobilized on metallic membranes as compared to the temperature optimum of the free enzyme.

The reducing sugar content of each feed and permeate sample taken during dextrin hydrolysis was analyzed by taking 1 milliliter of suitably diluted sample containing between 5 and 100 micrograms per milliliter reducing sugar pipetted into clean, dry test tubes. One milliliter of Nelson's Alkaline Solution, described in the *Journal of Biological Chemistry*, Vol. 153, 357 (1944) was pipetted into each tube, and the tubes were placed in a boiling water bath for 20 minutes. The tubes were then placed in a cold water bath for 15 minutes. At the end of 15 minutes, the tubes were removed from the water bath and one milliliter of arsenomolybdate solution was pipetted into each tube. The tubes were vortexed during a 5 minute period. After 15 minutes, the contents of each tube were transferred to a 13×100 millimeter round, matched cuvette and the absorbance of each sample was measured at 520 nanometers and compared to a standard curve. One milliliter of sample buffer solution was used to prepare the sample blank. The temperature optimum for immobilized glucoamylase was found to be 60° C. as is shown in FIG. 5.

EXAMPLE V

To compare the activity of immobilized glucoamylase with that of free glucoamylase, a temperature optimum for free glucoamylase was determined. A one milligram per milliliter solution of glucoamylase was dissolved in a 0.05 molar acetate buffer solution in a temperature controlled water bath along with several test tubes containing one milliliter of a one percent corn dextrin solution dissolved in a 0.05 molar acetate buffer solution at pH 4.5. At various temperatures between 30° C. and 70° C., 100 microliters of the glucoamylase solution were added to test tubes containing the one percent dextrin solution and incubated for exactly one minute. The test tubes were then placed in a boiling water bath to stop enzyme activity. The dextrin solutions for each temperature were then analyzed for reducing sugar and total carbohydrate content. As for the immobilized enzyme, the temperature optimum for free glucoamylase was found to be 60° C. as is shown in FIG. 5. As can be seen from FIG. 5, the immobilized enzyme of Example IV exhibited a somewhat higher activity at lower temperatures. However, at temperatures above 60° C., the free enzyme showed greater activity than did the immobilized enzyme.

EXAMPLE VI

The pH optimum of immobilized glucoamylase was determined by dissolving 200 grams of corn dextrin in 20 liters of a 0.05 molar acetate buffer solution, varying pH between 3.0 and 7.0, at 45° C., and circulating the solution through the ultrafiltration membrane system.

Figure 6:
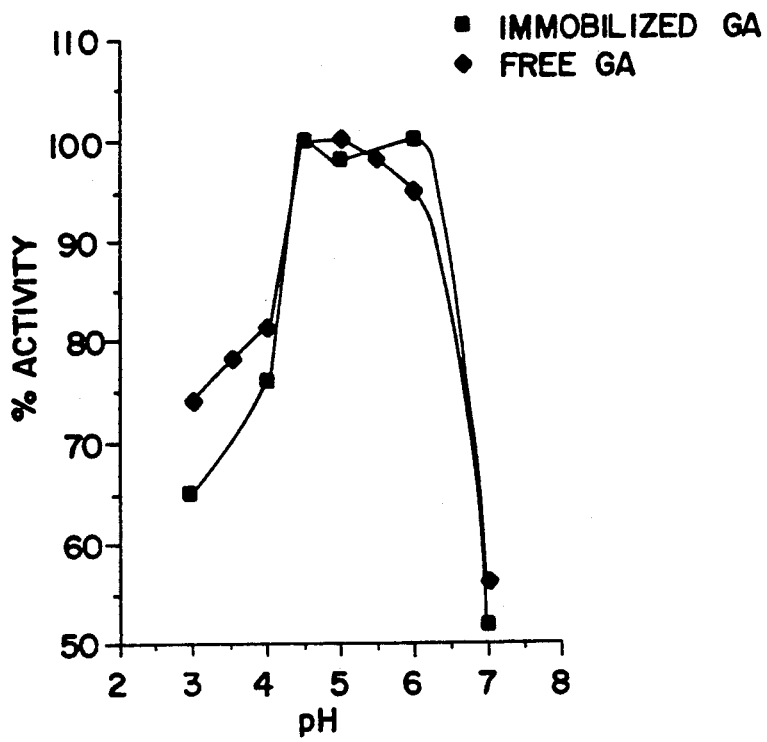
FIG. 6 graphically illustrates the pH optimum of glucoamylase immobilized on metallic membranes as compared to the pH optimum of the free enzyme.

The retentate line was recirculated to the steam jacketed feed tank and the permeate line was directed to a five-gallon plastic bucket where the permeates were collected. Permeate and retentate samples were taken at each pH and analyzed for reducing sugars and total carbohydrate by the methods described in Example IV. The pH optimum of immobilized glucoamylase showed a broad range from 4.5 to 6.0 as is shown in FIG. 6.

EXAMPLE VII

The pH optimum of free glucoamylase was determined by adding 100 microliters of a one milligram per milliliter solution of glucoamylase solubilized in a 0.05 molar acetate buffer solution to test tubes containing one milliliter of a one percent dextrin solution dissolved in a 0.05 molar acetate buffer solution at various pH's. The test tubes were incubated for one minute at 45° C. and then placed in a boiling water bath to stop enzyme activity. The dextrin solutions for each pH were then analyzed for reducing sugar and total carbohydrate content by the methods described in Example IV. As is shown in FIG. 6, the pH optimum of the free glucoamylase showed a range from 4.5 to 6.0, similar to that of the immobilized glucoamylase indicating that the pH optima of glucoamylase is essentially unchanged after immobilization.

EXAMPLE VIII

Figure 7:
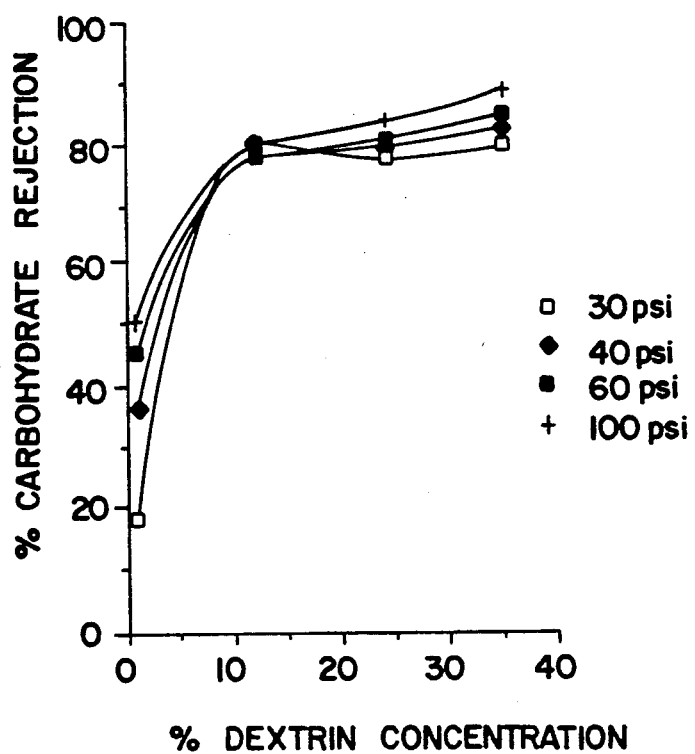
FIG. 7 graphically illustrates the degree of carbohydrate rejection of metallic membranes with immobilized glucoamylase at various pressures and dextrin concentrations.

The optimum pressure for maximum reducing sugar production was examined by solubilizing various concentrations of dextrin in 20 liters of 0.05 molar acetate buffer solution at pH 4.5 and 60° C. and circulating them through the ultrafiltration system at pressures between 30 psi and 100 psi. Permeate and retentate samples were taken at each pressure and dextrin concentration and analyzed for reducing sugar and total carbohydrate content by the techniques described in Example IV. As is seen in FIG. 7, carbohydrate rejection was not significantly affected by pressure for most dextrin concentrations. The rejection percentages for dextrin concentrations above one percent were consistently within the range of 80 percent to 90 percent. The rejection rate for the one percent dextrin solution was affected by the amount of pressure applied during hydrolysis, however, above 60 psi, the carbohydrate rejection was constant for all dextrin concentrations.

EXAMPLE IX

The degree of dextrin hydrolysis was calculated by determining the dextrose equivalents (DE) of each feed and permeate sample. Dextrose equivalents were calculated as $$\frac{\text{Reducing sugars}}{\text{Total carbohydrates}} \times 100 = DE$$

Figure 8:
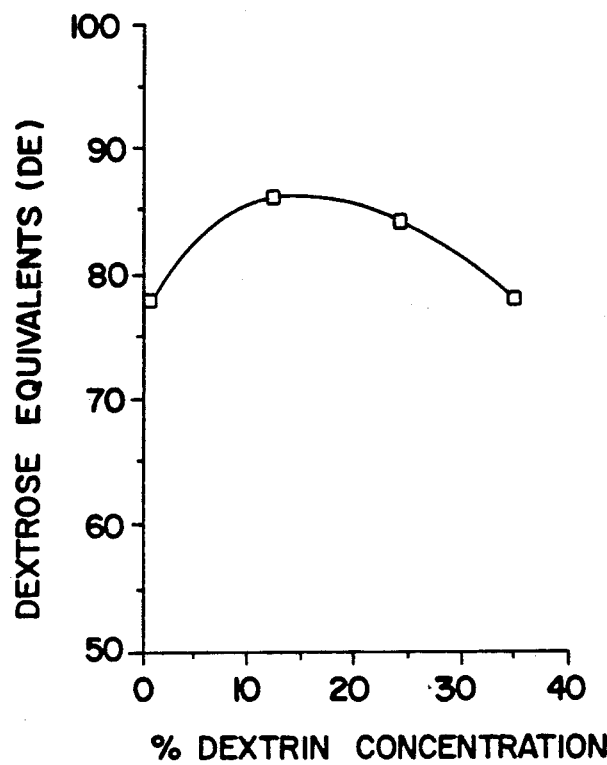
FIG. 8 graphically illustrates the change in dextrose equivalents of permeates taken during dextrin hydrolysis at 60 psi by immobilized glucoamylase at various feed concentrations.

Dextrose equivalents is a percentage measurement which represents the degree of hydrolysis in a dextrin or starch solution. Most starch and dextrin solutions contain very little reducing sugars and, therefore, have a low DE. By comparing the DE's of the feed and permeate samples, the degree of dextrin hydrolysis and, hence, glucoamylase activity was calculated. The average DE of the permeates of Example VIII taken during dextrin hydrolysis for the various dextrin concentrations at 60 psi was not significantly affected by the concentration of dextrins in the feed solution as is shown in FIG. 8. The rate of hydrolysis was constant, and the amount of reducing sugar produced was limited by the diffusion of substrate through the membrane.

EXAMPLE X

Figure 9:
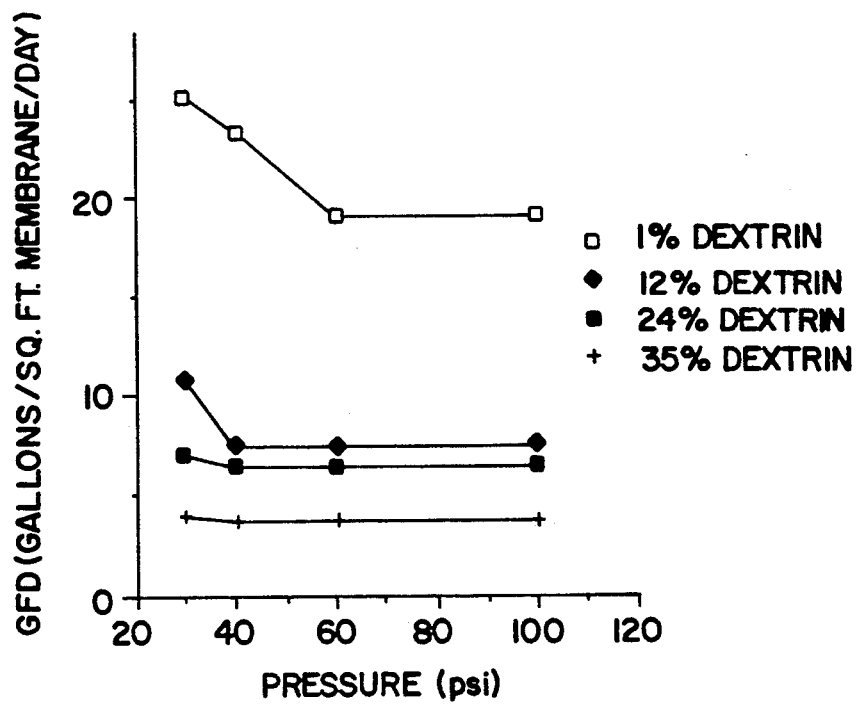
FIG. 9 graphically illustrates the effect of pressure on the flux of metallic membranes with immobilized glucoamylase at various dextrin feed concentrations.

The effect on membrane flux defined in terms of gallons per square foot of membrane per day was determined for various dextrin feed concentrations and operational pressures under the conditions of Example VIII. As is shown in FIG. 9, the membrane was greatly affected by both dextrin concentration and pressure. The steady state flux of the system was constant for each dextrin concentration above 60 psi. The effect of pressure on steady state flux was less for high dextrin concentrations.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not intended to be limitative of the invention so further described in such appended claims.

That which is claimed is:

1. A process for chemically converting a substrate into reaction products and physically separating said reaction products by size, said process comprising the steps of:
   a) providing an elongated tubular rigid porous housing with an inside wall and an outside wall, said housing having ultrafiltration metallic membrane secured along said inside wall, said membrane having an inner surface, an outer surface and pores, said outer surface of said membrane being secured to said inside wall of said housing;
   b) immobilizing an enzyme on said inner surface of said membrane by chelation of said enzyme to said membrane; and
   c) tangentially flowing a feed stream containing a substrate along said inner surface of said membrane through said housing so that said enzyme immobilized on said inner surface of said membrane catalyzes a chemical reaction of said substrate, converting said substrate into reaction products with sufficiently small reaction products filtering through said pores of said membrane and said housing and larger reaction products being retained by said membrane and said housing.

2. A method as defined in claim 1 wherein the enzyme is chelated onto said membrane at a pH approximately at the pH of the isoelectric point of said enzyme.

3. A method as defined in claim 1 wherein the enzyme is glucoamylase.

4. A method as defined in claim 1 wherein the enzyme is pectinase.

5. A method as defined in claim 1 wherein said feed stream passes through said tubular housing in a single pass.

6. A bioreactor for continuously chemically converting a substrate into reaction products and physically separating said reaction products by size, said bioreactor comprising:
   a) an elongated tubular rigid porous housing having an inside wall;
   b) a metal oxide ultrafiltration membrane having an inner surface, an outer surface and pores, said outer surface of said membrane being secured to said inside wall of said housing;

c) enzymes chelated onto said inner surface of said membrane;
d) means for tangentially flowing a feed stream containing a substrate along said inner surface of said membrane through said porous housing so that said substrate contacts said inner surface of said membrane and so that said enzymes chelated onto said inner surface of said membrane catalyze a chemical reaction of said substrate to chemically convert said substrate into reaction products and so that sufficiently small reaction products pass through said pores of said membrane and said housing and larger reaction products are retained by said membrane and within said inside wall of said housing.

7. The bioreactor set forth in claim 6 wherein the enzyme is glucoamylase.

8. The bioreactor set forth in claim 6 wherein the enzyme is pectinase.

* * * * *